(12) United States Patent
Priem (10) Patent No.: US 10,301,658 B2
(45) Date of Patent: May 28, 2019

(54) METHOD FOR IN VIVO PRODUCTION OF GLYCOSAMINOGLYCANS

(71) Applicants: CENTRE NATIONAL DE LA RECHERCHE SCIENTIFIQUE (CNRS), Paris (FR); UNIVERSITE GRENOBLE ALPES, St Martin d'Hères (FR)

(72) Inventor: Bernard Priem, Gieres (FR)

(73) Assignees: CENTRE NATIONAL DE LA RECHERCHE SCIENTIFIQUE (CNRS), Paris (FR); UNIVERSITE GRENOBLE ALPES, Saint Martin d'Heres (FR)

( * ) Notice: Subject to any disclaimer, the term of this patent is extended or adjusted under 35 U.S.C. 154(b) by 140 days.

(21) Appl. No.: 15/113,059

(22) PCT Filed: Jan. 23, 2015

(86) PCT No.: PCT/EP2015/051339
§ 371 (c)(1),
(2) Date: Oct. 25, 2016

(87) PCT Pub. No.: WO2015/110571
PCT Pub. Date: Jul. 30, 2015

(65) Prior Publication Data
US 2017/0137857 A1    May 18, 2017

(30) Foreign Application Priority Data
Jan. 23, 2014 (FR) .................... 14 50564

(51) Int. Cl.
| | |
|---|---|
| C12P 19/26 | (2006.01) |
| C08B 37/00 | (2006.01) |
| C12P 19/18 | (2006.01) |
| A23L 33/10 | (2016.01) |
| C12P 19/04 | (2006.01) |

(52) U.S. Cl.
CPC .............. *C12P 19/26* (2013.01); *A23L 33/10* (2016.08); *C08B 37/0063* (2013.01); *C08B 37/0069* (2013.01); *C08B 37/0075* (2013.01); *C12P 19/04* (2013.01); *C12P 19/18* (2013.01); *A23V 2002/00* (2013.01)

(58) Field of Classification Search
CPC .................................................. C07K 14/245
See application file for complete search history.

(56) References Cited

U.S. PATENT DOCUMENTS

| | | | | |
|---|---|---|---|---|
| 8,697,398 B2 * | 4/2014 | Doherty | ............... | C07K 14/245 435/84 |
| 2011/0244520 A1 * | 10/2011 | Doherty | ............... | C07K 14/245 435/84 |

FOREIGN PATENT DOCUMENTS

| | | |
|---|---|---|
| WO | 2008/035372 A2 | 3/2008 |
| WO | 2010136435 A1 | 12/2010 |

OTHER PUBLICATIONS

Priem et al. 2002; A new fermentation process allows large-scale production of human milk oligosaccharides by metabolically engineered bacteria. Glycobiology. 12(4): 235-240.*
Yavuz et al. 2008; Glucuronylation of Escherichia coli for the bacterial synthesis of the carbohydrate moiety of nonsulfated HNK-1. Glycobiology. 18(2): 152-157.*
Barreteau et al. (2012) Carbohydrate Research, 1:360:19-24.
Blumenkrantz et al. (1973) Analytical biochemistry, 54:484-489.
Cimini et al. (2010) Appl. Microbiol, and Biotechnol, 85(6):1779-1787.
Hodson et al. (2000) J. Biol. Chem., 275(35): 27311-5.
Inoue et al. (1990) Gene, 96:23- 28.
Jin et al. (2011) Biosci. Biotechnol. Biochem., 75(7), 1283-1289.
Kakuda et al. (2004) J. Biol. Chem., 279 (21), pp. 22693-22703.
Krahulec et al. (2005) Molecular Biology, 30:129-134.
Manzoni et al. (1996) J. Bioactive and Compatible Polymers, vol. 11, p301.
Morgan et al. (1955) Biochem. Journal, 61(4):586-589.
Ninomiya et al. (2002) J. Biol. Chem., Jun. 14;277(24):21567-75.
Priem et al. (2002) Glycobiology. vol. 12 No. 4pp. 235-240.
Schiraldi et al. (2010) Appl. Microbiol, and Biotechnol, 87:1209-1220.
Wang et al. (2011) Bioengineered Bugs, 2:1, 63-67 (Jan./Feb.).
Whiffield (2006) Annual Review of Biochemistry, 75:39-68.
Yamada and Sugahara (2008) Current Drug Discovery Technologies, 5, 289-301.
Yavuz et al. (2008) Glycobiology, 18(2):152-157.
Zanfardino et al. (2010) Microbiol. Cell Factories, 9:34.
Julie A Robinson; Robinson H Clem—Initiation of chondroitin sulphate synthesis by beta-D-galactosides—Substrates for galactosyltransferase II—The Biochemical Journal, May 1, 1985—vol. 227, Nr:3, pp. 805-814.

(Continued)

*Primary Examiner* — Karen Cochrane Carlson
(74) *Attorney, Agent, or Firm* — Arrigo, Lee, Guttman & Mouta-Bellum LLP (57) ABSTRACT

The present invention relates to a method for in vivo production of glycosaminoglycans (GAG), by metabolic engineering in a genetically modified cell. In a method according to the invention, said cell is genetically modified in order to express the genes coding for the enzymes that are suitable for synthesizing GAG from an exogenous precursor, preferably internalized by the cell. According to one specific feature, the present invention relates to a method for producing chondroitin or heparosan in a genetically modified bacterial cell, from an exogenous beta-galactoside precursor, preferably internalized by the cell. According to another specific feature, the present invention relates to the use of an *Escherichia coli* cell comprising at least the genes glcA-T, kfoC, kfiD and wbpP for the production of chondroitin. According to yet another specific feature, the present invention relates to the use of an *Escherichia coli* cell comprising at least the genes glcA-T, kfiA, kfiB, kfiC and kfiD for the production of heparosan. The present invention also relates to the use of the obtained glycosaminoglycans by implementing a method according to the invention in order to prepare a drug, a food composition or a cosmetic product.

11 Claims, 5 Drawing Sheets

Specification includes a Sequence Listing.

(56) References Cited

OTHER PUBLICATIONS

Bradbeer M; Robinson J A; Robinson H C—The mechanism of initiation of chondroitin sulphate synthesis by beta-D-galactosides—Medline, Sep. 1, 1990; US National Library of Medicine (NLM), Bethesda, MD, US.

Mikami Tadahisa; Kitagawa Hiroshi—Biosynthesis and function of chondroitin sulfate—Biochimica et Biophysica Acta (BBA)—General Subjects Elsevier, Amsterdam, NL.

Chunyu Zhang; Long Liu; Liping Teng; Jinghua Chen; Jian Liu; Jianghua Li; Guocheng Du; Jian Chen—Metabolic engineering of *Escherichia coli* BL21 for biosynthesis of heparosan, a bioengineered heparin precursor—Metabolic Engineering, Sep. 1, 2012 Academic Press—ISSN 1096-7176—vol. 14, Nr:5, pp. 521-527.

Deangelis P L—Microbial glycosaminoglycan glycosyltransferases—Glycobiology, Jan. 1, 2002 Oxford University Press, US—ISSN 0959-6658 vol. 12, Nr:1, pp. 9R-16R.

Paul L DeAngelis—Glycosaminoglycan polysaccharide biosynthesis and production: today and tomorrow—Applied Microbiology and Biotechnology, Mar. 6, 2012 Springer, Berlin, DE—ISSN 1432-0614—vol. 94, Nr2, pp. 295-305.

* cited by examiner

Figure 7

METHOD FOR IN VIVO PRODUCTION OF GLYCOSAMINOGLYCANS

The present invention relates to a method for producing glycosaminoglycan (GAG) in vivo, by metabolic engineering in a genetically modified cell. In a method according to the invention, said cell is genetically modified in order to express the genes encoding the enzymes suitable for synthesizing GAG from a precursor exogenous to the cell, and preferably an exogenous precursor internalized by said cell. In a particular aspect, the present invention relates to a method for producing chondroitin or heparosan in a genetically modified bacterial cell, from an exogenous beta-galactoside precursor, preferably internalized by the cell. In another particular aspect, the present invention relates to the use of an *Escherichia coli* cell comprising at least the genes glcA-T, kfoC, kfiD and wbpP for producing chondroitin. In another particular aspect, the present invention relates to the use of an *Escherichia coli* cell comprising at least the genes glcA-T, kfiA, kfiB, kfiC and kfiD for producing heparosan. The present invention also relates to the use of glycosaminoglycan obtained by implementing a method according to the invention for the preparation of a medicinal product.

Glycosaminoglycans (GAGs) are heteropolysaccharides which make up the extracellular matrix. They consist of a repeating disaccharide unit composed of, on the one hand, a hexosamine, which can be N-acetylglucosamine or N-acetylgalactosamine, and, on the other, a uronic acid, which can be glucuronic acid or iduronic acid, or a galactose. These units can be sulfated. GAGs are highly negatively charged due to the presence of sulfate or carboxyl groups on most of their sugars, which gives them viscosity-enhancing properties, they play a role in connective tissue maintenance and they are also involved in cell recognition and tissue growth. According to the composition of the disaccharide unit, one distinguishes among GAGs: hyaluronic acid, chondroitin, chondroitin sulfate, dermatan sulfate, heparan sulfate, heparin, heparosan and keratan sulfate. Chondroitin is a precursor of chondroitin sulfates and dermatan sulfates (Cimini et al., 2010). In vivo, chondroitin is subjected during its polymerization to many sulfations, catalyzed by chondroitin sulfotransferases, which result in the formation of O-sulfated groups in various positions. According to the position of these sulfate groups, chondroitin sulfates play different roles.

GAGs can be used in various therapeutic fields. Their best known application is the treatment of osteoarthritis, they have anti-inflammatory activity and action in cartilage regeneration. More recently, it was shown that chondroitin sulfates have antiviral and anti-infective effects, they are also used in tissue regeneration and engineering. Chondroitin sulfates are also studied for their utility in diagnosing and treating cancer (Jin et al., 2008; Yamada and Sugahara, 2011). Moreover, chondroitin can be used as nutritional adjuvant. Heparosan, the skeleton of which is a precursor of heparin synthesis, can be used in various therapeutic applications, as a precursor for non-animal heparin or heparin-like products, but also for vectorization of therapeutic products.

GAGs can be extracted from animal sources or synthesized chemically, enzymatically or microbiologically. The synthesis of these compounds by traditional organic chemistry, however, remains very difficult today. Chondroitin sulfate and hyaluronic acid can be extracted and purified from animal tissue such as shark fin, fish cartilage or animal carcasses. The use, in particular the therapeutic use, of these compounds requires high and constant levels of quality and purification which extraction cannot fully meet, in particular due to the risk of contamination of GAGs extracted from animal tissues, for example by a virus or a prion (Zanfardino et al., 2010; Wang et al., 2011).

Another source of GAGs is extraction from certain pathogenic bacteria, where they are part of the extracellular capsule, which gives them a natural barrier role with regard to host defenses. The production of chondroitin from capsular polysaccharides (CPSs) has already been carried out from *E. coli* K4 and K5 pathogenic strains (Schiraldi et al., 2010; Inoue et al., 1990). However, most therapeutic uses of chondroitin require a size of 14 to 20 kDa (Schiraldi et al., 2010). The average sizes of wild-type CPSs are about 650 kDa and those of GAGs produced by metabolic engineering are about 150 kDa (Krahulec et al., 2005); the chondroitin thus obtained must therefore be depolymerized prior to most of its therapeutic uses. This depolymerization step decreases the homogeneity and the quality of the product from a therapeutic perspective.

There is thus currently a need to have a method for producing glycosaminoglycans having a quality and in an amount suitable for therapeutic use in particular. That is now the subject-matter of the present invention.

The Inventors have in fact developed a method of engineering by genetic modification a cell for producing glycosaminoglycans, and in particular chondroitin and heparosan, from an exogenous acceptor of the beta-galactoside type. This exogenous acceptor having two saccharide units replaces the natural bacterial acceptor, or "endogenous" acceptor. According to an embodiment of the invention, said "exogenous acceptor" can be internalized by the cell. According to another embodiment of the invention, said "exogenous acceptor" can be the object of intracellular synthesis by a recombinant beta-galactosyltransferase.

The state of the art does not disclose beta-galactoside as a possible acceptor for enzymes having GAG synthesis activity. Biosynthesis of bacterial glycosaminoglycans has its origin in the bacterial cytoplasm, in the vicinity of the membrane by which they transit in order to integrate into the extracellular wall, from an endogenous membrane acceptor, in all likelihood diacylglycerophosphate (Whitfield, 2006). It has been shown in an in vitro bacterial expression system that by adding in the reaction medium oligosaccharides the minimum size of which is six saccharide units, and in the presence of the nucleotide sugars UDP-GlcA and UDP-GalNAc, K-4 chondroitin polymerase KfoC from *Escherichia coli*, which has both GlcA-transferase and GalNAc-transferase activities, is able to produce a polysaccharide having a size of about 20 kDa (Ninomiya et al., 2002). WO 01/04341 and Priem et al. (2002) disclose the production of oligosaccharides in a bacterial strain capable of integrating an exogenous precursor. Yavuz et al. (2008) disclose the production of glucuronidated oligosaccharides in *E. coli*. Doherty et al. (US2011/0244520) have disclosed a method for producing chondroitin in a bacterial strain using a set of exogenous genes, but in the absence of an exogenous precursor.

Figure 1:
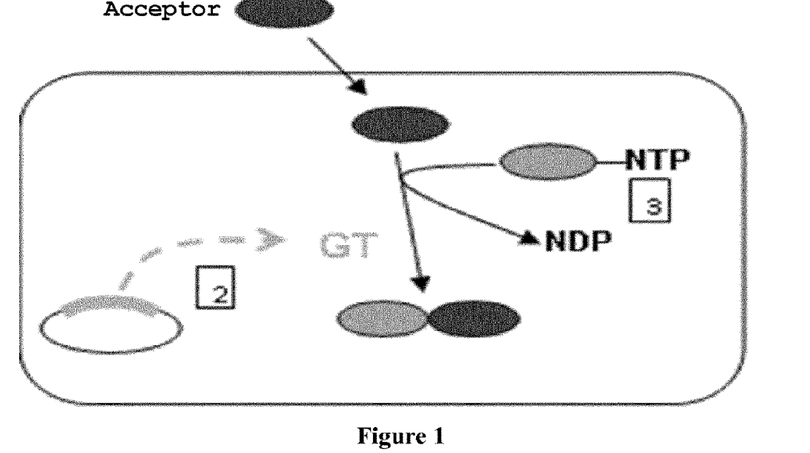
FIG. 1: Overall diagram of the metabolic engineering of the genetically modified cells. After the entry of an acceptor in the bacterium: heterologous expression of the glycosyltransferase of interest (step 2), accumulation of sugar nucleotides, substrates of glycosyltransferases (step 3).
Figure 2:
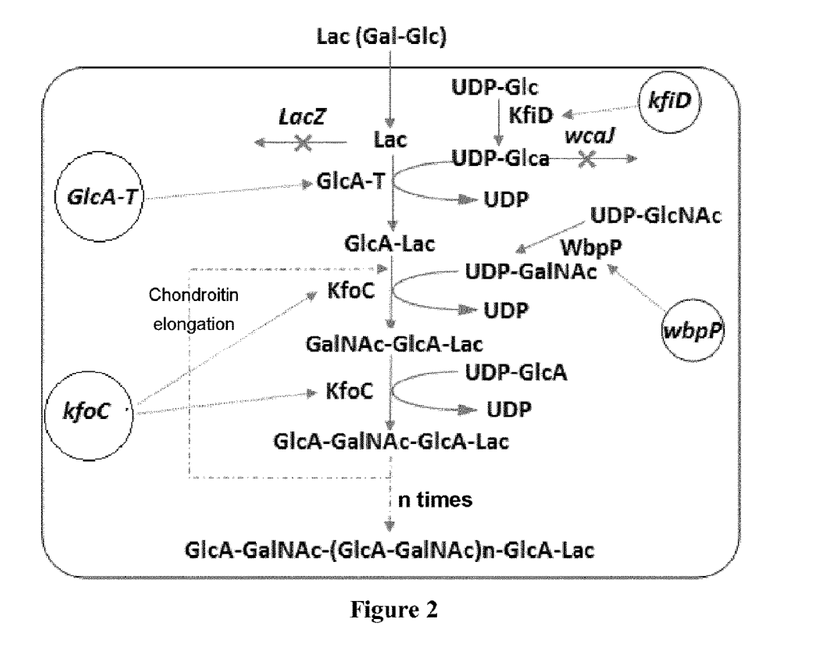

The Inventors have now shown that, subject to the presence in the bacterium of a glycosyl beta-galactoside and at least one enzyme having an activity of synthesizing a GAG from glycosyl beta-galactoside, it is possible to carry out the synthesis by metabolic engineering of GAG of reduced polydispersity and of size suitable for therapeutic use (FIGS. 1 and 2). In particular, the Inventors have shown the possibility of producing chondroitin, by metabolic engineering, subject to the presence in the bacterium of a glucuronyl beta-galactoside and a bacterial chondroitin synthase, and in the presence of an exogenous beta-galactoside acceptor. The Inventors have also shown that in the presence of an exogenous beta-galactoside acceptor and at least one gene encoding an enzyme capable of synthesizing heparosan, and preferably the genes kfiA, kfiB, kfiC and kfiD, it is possible to produce heparosan, with a yield superior to the yields obtained by the implementation of known methods.

Synthesis of GAG from an exogenous acceptor by a method according to the invention has the advantage of making it possible to transpose the biosynthetic pathway to various cell types capable of internalizing said exogenous precursor. Hence, the presence of the endogenous membrane acceptor specific to *E. coli* or to GAG-producing pathogenic bacterial strains is not necessary. The GAG thus produced is characterized by the presence at the chain terminus of the exogenous beta-galactoside precursor, this motif being similar to a motif naturally present in man (Kakuda et al., 2004).

A method for producing GAG metabolically according to the invention also has an economic advantage due to the low cost of the exogenous precursor used.

The invention will be now disclosed in detail and illustrated by way of examples.

The present invention relates to a method for producing glycosaminoglycan (GAG) in a genetically modified cell, said method comprising the following steps:
1) obtaining a cell comprising at least:
   an exogenous gene encoding an enzyme capable of exerting a glycosyltransferase activity on a beta-galactoside substrate, and the elements enabling the expression of said gene in said cell and the synthesis of glycosyl beta-glucuronide,
   a gene encoding an enzyme capable of synthesizing said glycosaminoglycan from glycosyl beta-galactoside, or the genes encoding the enzymes of the synthetic pathway of said glycosaminoglycan from glycosyl beta-galactoside, and the elements enabling the expression of said gene(s) in said cell,
   a gene encoding an enzyme capable of ensuring the internalization of exogenous beta-galactoside by the cell, and the elements enabling the expression of said gene in said cell, and
2) culturing said cell in the presence of exogenous beta-galactoside and under conditions compatible with the production of said GAG by the cell.

The term "glycosaminoglycan" (GAG) refers to a heteropolysaccharide consisting of a repeating disaccharide unit composed of a hexosamine and a uronic acid or a galactose. In a particular aspect, a method according to the invention relates to the production in a genetically modified cell of a GAG selected from the group consisting of: hyaluronic acid, chondroitin, chondroitin sulfate, dermatan, dermatan sulfate, heparan, heparan sulfate, heparin, heparosan, keratan and keratan sulfate.

The term "genetically modified cell" refers to a microorganism the genome sequence of which has been subjected to at least one alteration, addition or deletion, in order to confer a particular phenotype on said cell. This modification can in particular be made by the addition of at least one exogenous gene and the elements enabling the expression of this gene in said cell. In a particular aspect of a method according to the invention, said cell is genetically modified by the introduction of at least one exogenous gene carried on a plasmid. In another particular aspect of a method according to the invention, said cell is genetically modified by the introduction of at least one exogenous gene integrated into the genome of said cell.

The term "exogenous beta-galactoside" refers to a precursor compound, internalized by said cell or a subject of intracellular synthesis by a recombinant beta-galactosyltransferase, intervening in the biosynthetic pathway of GAG and substrate for an enzyme having glycosyltransferase activity, preferably glucuronyltransferase activity.

The term "exogenous gene" refers to a heterologous nucleic acid, not naturally present in the cell, the nucleotide sequence of which encodes a defined protein. Said nucleic acid can be DNA, in single-stranded or double-stranded form, or RNA. Into a method according to the invention, said exogenous gene is introduced into said cell by techniques well-known to persons skilled in the art specializing in the handling of recombinant nucleic acids, such as, for example, heat shock or electroporation.

The term "the elements enabling the expression of said gene in said cell" refers in particular to a promoter, signals for translation initiation and termination, as well as suitable transcription regulation regions. According to a preferred embodiment of the invention, the nucleic acid sequence is introduced into said cell in the form of an expression vector which comprises said elements enabling the expression of said gene in said cell. An expression vector can also comprise one or more elements which maintain it in the cell, in a stable manner over successive generations. These elements are selected according to the host cell used, and can be in particular a gene encoding antibiotic resistance. Said vector can replicate autonomously or be integrated into the host cell genome. According to a particular embodiment of the invention, the expression vector is present in the form of a plasmid, a plasmid which can carry one or more exogenous genes of interest for implementing a method according to the invention. Each plasmid present in the cell can be characterized by the number of copies of said plasmid in the cell. In a particular aspect of a method according to the invention, a plasmid carrying at least one exogenous gene of interest for implementing a method according to the invention is present in low copy number. In another particular aspect of a method according to the invention, a plasmid carrying at least one exogenous gene of interest for implementing a method according to the invention is present in high copy number. It is well-known to persons skilled in the art that the level of expression of a gene can be correlated with the copy number of the gene in the cell.

The expression "enzymes of the synthetic pathway of said glycosaminoglycan from glucuronyl beta-galactoside" refers to the various enzymes capable of exerting an activity on the GAG synthesis pathway in the cell.

In a particular aspect of a method according to the invention, said exogenous beta galactoside is present in the culture medium. In another particular aspect of a method according to the invention, said exogenous beta-galactoside is recombinant beta-galactoside, produced by said genetically modified cell, said genetically modified cell comprising at least one exogenous gene enabling the synthesis of beta-galactoside. According to a preferred embodiment of a method according to the invention, the beta-galactoside is selected from the group consisting of the beta-galactosides handled by the bacterial active transport system, and preferably from the group consisting of: lactose, lactose-allyl, beta-allylgalactoside, beta-methylgalactoside, allyl beta-galactoside, propargyl beta-galactoside.

In a particular aspect of a method according to the invention, the genetically modified cell is cultured in the presence of exogenous beta-galactoside, said exogenous beta-galactoside being added during the culture in such a way that the glycosyl-beta-glucuronide, obtained by the transfer of a glucuronyl group to the beta-galactoside, is present in the intracellular compartment of the cell during most of the culture, and preferably throughout the culture. The beta-galactoside can be added to the culture from time to time or dropwise. The beta-galactoside can be added to the culture at a concentration between about 0.5 and about 8 g/l, the term "about" expressing a variation on the order of 10%, preferably between about 0.6 and about 7 g/l, preferably between about 1 and about 5 g/l, and more preferably between about 1.5 and about 4 g/l.

The invention also relates to a method for producing GAG in a genetically modified cell according to the invention wherein the enzyme capable of ensuring the internalization by the cell of exogenous beta-galactoside is a permease, preferably a permease specific to lactose, preferably the beta-galactoside permease encoded by the *E. coli* LacY gene.

In a method for producing GAG in a genetically modified cell according to the invention, said cell is cultured according to a method well-known to persons skilled in the art, who can implement the culture method and select the composition of the culture medium, in particular the concentration of nutritive elements, and the culture parameters, such as temperature, pH, oxygen concentration and culture inoculation, according to their general knowledge. The culture medium can in particular include at least one source of one or more elements selected from: sugars, carbon, nitrogen, phosphate, magnesium, calcium and vitamins. In a method according to the invention, the culture can be prepared in a fermentor according to a conventional fermentation method selected from: batch culture, fed-batch culture or continuous culture. Preferably, in a method according to the invention, the genetically modified cell is cultured in fed-batch mode.

The invention also relates to a method for producing GAG in a genetically modified cell according to the invention, wherein the enzyme capable of exerting a glycosyltransferase activity is a glucuronyltransferase. According to a particular embodiment of a method according to the invention, the glucuronyltransferase is a mammalian glucuronyltransferase. Preferably, the mammalian glucuronyltransferase selected is a rat glucuronyltransferase or a mouse glucuronyltransferase, and preferably mouse brain glucuronyltransferase.

In an even more particular aspect, the invention relates to a method for producing glycosaminoglycans (GAGs) in a genetically modified cell according to the invention, wherein the gene encoding an enzyme capable of exerting a glycosyltransferase activity on a beta-galactoside substrate is the gene glcA-T (encoding mouse beta-1-3-glucuronyltransferase (GenBank GI number: 568960207 of 27 Dec. 2013).

According to a particular embodiment, the invention relates to a method for producing GAG in a genetically modified cell, characterized in that the GAG is produced in the cytoplasm of said cell.

The invention also relates to a method for producing GAG in a genetically modified cell according to the invention, wherein said cell further comprises a gene encoding an enzyme capable of synthesizing UDP-GlcA from UDP-Glc, and the elements enabling the expression of said gene in said cell. According to a particular embodiment of the invention, the enzyme capable of synthesizing UDP-GlcA from UDP-Glc is UDP-glucose dehydrogenase.

The invention also relates to a method for producing GAG in a genetically modified cell according to the invention, wherein said genetically modified cell further comprises a gene encoding an enzyme capable of synthesizing UDP-GalNAc, and the elements enabling the expression of said gene in said cell. According to a particular embodiment of the invention, the enzyme capable of synthesizing UDP-GalNAc is UDP-N-acetylglucosamine epimerase from *Pseudomonas aeruginosa*. According to another particular embodiment, the enzyme capable of synthesizing UDP-GalNAc is UDP-GlcNAc/Glc 4-epimerase (EC:5.1.3.2) from *Campylobacter jejuni* subsp. *jejuni* NCTC 11168=ATCC 700819, entered under K01784, UDP-glucose 4-epimerase (EC:5.1.3.2).

The invention also relates to a method for producing GAG in a genetically modified cell according to the invention wherein at least one gene of said genetically modified cell encoding an enzyme using UDP-glcA for the synthesis of a cellular product is inactivated. According to a particular embodiment of the invention, said cell is an *Escherichia coli*-type bacterium and the wcaJ gene encoding the enzyme using UDP-glcA for the synthesis of colanic acid is inactivated.

The invention also relates to a method for producing GAG in a genetically modified cell according to the invention wherein at least one gene of said genetically modified cell encoding an enzyme capable of hydrolyzing beta-galactoside is inactivated. According to a particular embodiment of the invention, said cell is an *Escherichia coli*-type bacterium and the enzyme capable of hydrolyzing beta-galactoside the gene of which is inactivated is beta-galactosidase encoded by the LacZ gene.

The invention also relates to a method for producing GAG in a genetically modified cell according to the invention wherein said cell is selected from bacteria and recombinant eukaryotic organisms.

The invention also relates to a method for producing GAG in a genetically modified cell according to the invention wherein said genetically modified cell is selected from the group consisting of: *Escherichia coli, Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae, Neisseria meningitis, Saccharomyces cerevisiae, Saccharomyces pombe, Candida albicans* and *Corynebacterium glutamicum*.

According to a preferred embodiment of the invention, said genetically modified cell is an *Escherichia coli* strain bacterium. According to a more preferred embodiment of the invention, said genetically modified cell is an *Escherichia coli* nonpathogenic strain bacterium. More particularly, said genetically modified cell is selected from the group consisting of: the *Escherichia coli* strain K12, the *Escherichia coli* K12 strain DH1 (ATCC number: 68153), the *Escherichia coli* K12 strain DH1 wherein the lacZ and wcaJ genes are inactivated (Yavuz et al., 2008), a group B *Escherichia coli* strain, preferably *Escherichia coli* BL21.

According to another preferred embodiment of the invention, said genetically modified cell is a yeast.

According to a particular embodiment, the invention relates to a method for producing GAG in a genetically modified cell, characterized in that said GAG is chondroitin.

According to a particular embodiment, the invention relates to a method for producing chondroitin in a genetically modified cell, said method comprising:

1) obtaining a cell comprising at least one exogenous gene encoding an enzyme capable of exerting a glycosyltransferase activity on a beta-galactoside substrate, a gene encoding an enzyme capable of synthesizing chondroitin from glycosyl beta-glucuronide, a gene encoding an enzyme capable of ensuring the internalization by the cell of exogenous beta-galactoside, and 2) culturing the cell in the presence of exogenous beta-galactoside and under conditions compatible with the production of chondroitin.

The term "chondroitin" refers to a GAG having as disaccharide unit an N acetylgalactosamine (GalNAc) and a glucuronic acid (GlcA) and can be represented by: "4-GlcA-β-1,3-GalNAc-β-1".

According to an even more particular embodiment, the invention relates to a method for producing chondroitin in a genetically modified cell according to the invention, wherein said exogenous beta-galactoside is lactose.

According to an even more particular embodiment, the invention relates to a method for producing chondroitin in a genetically modified cell according to the invention, wherein the enzyme capable of exerting a glycosyltransferase activity on a beta-galactoside substrate is a glucuronyltransferase, preferably a mammalian glucuronyltransferase.

The invention also relates to a method for producing chondroitin in a genetically modified cell wherein the enzyme capable of synthesizing chondroitin is a bacterial synthase capable of synthesizing chondroitin from glucuronyl-lactose. In an even more particular aspect, the invention relates to a method for producing chondroitin in a genetically modified cell wherein the gene encoding an enzyme capable of exerting a chondroitin synthesis activity is the kfoC gene encoding chondroitin polymerase from the $E.$ $coli$ PMV-1 strain K4 (GenBank number: GI: 21326784 of 20 Dec. 2010).

According to another particular embodiment, the invention relates to a method for producing GAG in a genetically modified cell, characterized in that said GAG is heparosan.

According to a particular embodiment, the invention relates to a method for producing heparosan in a genetically modified cell, said method comprising:
  obtaining a cell comprising at least one exogenous gene encoding a mammalian enzyme capable of exerting a glycosyltransferase activity on a beta-galactoside substrate, the genes encoding the enzymes of the synthetic pathway of said glycosaminoglycan from glycosyl beta-galactoside, and the elements enabling the expression of said genes in said cell, a gene encoding an enzyme capable of ensuring the internalization by the cell of exogenous beta-galactoside, and
  culturing said cell in the presence of exogenous beta-galactoside, and under conditions compatible with the production of heparosan by said cell.

The term "heparosan" refers to a bacterial glycosaminoglycan composed of regular repeating units of 4-β-glucuronyl-(1-4)-α-N-acetylglucosaminyl-1. Heparosan is produced by pathogenic bacteria such as $Escherichia$ $coli$ K5 and $Pasteurella$ $multocida$ and is found in the bacterial capsule.

According to another even more particular embodiment, the invention relates to a method for producing heparosan in a genetically modified cell according to the invention, characterized in that said beta-galactoside is lactose.

According to another even more particular embodiment, the invention relates to a method for producing heparosan in a genetically modified cell according to the invention, characterized in that said beta-galactoside is allyl-lactose.

In a particular aspect, the invention relates to a method for producing chondroitin in a genetically modified cell according to the invention, the method comprising obtaining an $Escherichia$ $coli$ strain K12 cell, comprising at least:
  a gene encoding a mammalian glucuronyltransferase, and the elements enabling the expression of said gene in said cell,
  a gene encoding a bacterial chondroitin synthase, and the elements enabling the expression of said gene in said cell,
  a gene encoding a beta-galactoside permease, and the elements enabling the expression of said gene in said cell,
and culturing said cell in the presence of exogenous beta-galactoside and under conditions compatible with the production of chondroitin by the cell.

In an even more particular aspect of the invention, the method for producing chondroitin comprises obtaining an $Escherichia$ $coli$ strain K12 cell, comprising at least:
  a gene encoding mouse glucuronyltransferase, and the elements enabling the expression of said gene in said cell,
  a gene encoding chondroitin synthase kfoC from $E.$ $coli$ K4, and the elements enabling the expression of said gene in said cell,
  a gene encoding a lactose permease, and the elements enabling the expression of said gene in said cell,
  a gene encoding a UDP-glucose dehydrogenase, and
  a gene encoding the UDP-N-acetylglucosamine epimerase from $Pseudomonas$ $aeruginosa$,
and culturing said cell in the presence of exogenous beta-galactoside and under conditions compatible with the production of said GAG by the cell.

In an even more particular aspect, the invention relates to a method for producing chondroitin in a genetically modified cell, said method comprising obtaining an $Escherichia$ $coli$ strain K12 cell, said cell comprising at least the genes glcA-T (GI: 568960207), kfoC (GI: 21326784), kfiD (UDP-glucose-6-dehydrogenase, $E.$ $coli$, GI 735963 of 23 Oct. 2008) and wbpP ($Pseudomonas$ $aeruginosa$, GI: 6690131 of 12 Jan. 2000), and culturing said cell in the presence of exogenous lactose and under conditions compatible with the production of chondroitin by the cell.

The invention also relates to a method for producing heparosan in a genetically modified cell according to the invention, comprising obtaining a cell comprising at least: a gene encoding an enzyme capable of exerting a glycosyltransferase activity on a beta-galactoside substrate, the genes encoding the enzymes of the synthetic pathway of said glycosaminoglycan from glycosyl beta-galactoside, and the elements enabling the expression of said gene(s) in said cell, a gene encoding an enzyme capable of ensuring the exogenous internalization of beta galactoside by the cell, and the elements enabling the expression of said gene in said cell, and culturing said cell in the presence of exogenous beta-galactoside and under conditions compatible with the production of heparosan by the cell.

According to an even more particular embodiment, the invention relates to a method for producing heparosan in a genetically modified cell according to the invention, wherein said exogenous beta-galactoside is lactose.

According to an even more particular embodiment, the invention relates to a method for producing heparosan in a genetically modified cell according to the invention, wherein the enzyme capable of exerting a glycosyltransferase activity on a beta-galactoside substrate is a glucuronyltransferase, preferably a mammalian glucuronyltransferase. The invention more particularly relates to a method for producing heparosan in a genetically modified cell according to the invention, comprising obtaining a cell comprising at least one exogenous gene encoding a GlcNAc transferase, an exogenous gene encoding a GlcA transferase, and an exogenous gene encoding a UDP-Glc dehydrogenase.

According to an even more particular embodiment, the invention also relates to a method for producing heparosan in a genetically modified cell according to the invention, comprising obtaining an *Escherichia coli* strain cell, and preferably a strain K12 cell, said cell comprising at least:
- the glcA-T gene (GI 568960207 of 27 Dec. 2013),
- the kfiA gene (GI: 496605 of 23 Oct. 2008) which encodes a GlcNAc transferase,
- the kfiB gene (SEQ ID NO: 1) which encodes a protein whose role is unknown at present,
- the kfiC gene which encodes a glcA transferase (GI: 735964 of 23 Oct. 2008),
- the kfiD gene which encodes a UDP-glucose 6-dehydrogenase (GI: 735963 of 23 Oct. 2008), and culturing said cell in the presence of a beta-galactoside selected from: lactose and allyl lactose, under conditions compatible with the production of heparosan by the cell.

According to an even more particular embodiment, the invention also relates to a method for producing heparosan in a genetically modified cell according to the invention, comprising obtaining an *Escherichia coli* strain cell, and preferably an *Escherichia coli* strain K12 cell, said cell comprising at least the gene encoding a mammalian beta-1,3-glucuronyltransferase and the sequence whose reference number is X77617.1 (23 Oct. 2008) which comprises the kfiD, kfiC, kfiB and kfiA genes of *E. coli*, and culturing said cell in the presence of a beta-galactoside selected from: lactose and allyl lactose, under conditions compatible with the production of heparosan by the cell.

According to an even more particular embodiment, the invention also relates to a method for producing heparosan in a genetically modified cell according to the invention, comprising obtaining an *Escherichia coli* strain cell, and preferably an *Escherichia coli* strain K12 cell, said cell comprising at least a) the glcA-T gene, and b) the kfiA, kfiB, kfiC and kfiD genes of *E. coli* or at least one gene encoding a protein having a function homologous to that of an protein encoded by kfiA, kfiB, kfiC or kfiD, and culturing said cell in the presence of a beta galactoside selected from: lactose and allyl lactose, under conditions compatible with the production of heparosan by the cell.

By "protein having a homologous function" is meant a protein exerting a function or an activity of comparable nature. The functions or activities of two or more proteins can be regarded as homologous according to the result of tests wherein these proteins are placed under identical reaction conditions and the same parameter is evaluated, for example the appearance of the given product of an enzymatic reaction. Proteins having a homologous function will produce the same product.

In a method according to the invention, a gene encoding a protein having a function homologous to that of a protein encoded by kfiA, kfiB, kfiC or kfiD can in particular be a homologous gene from another bacterial strain, such as for example *Pasteurella multocida*, and in particular the PmHS1 gene which encodes a protein having dual GlcAT and GlcNAcT activity.

The implementation of a method according to the invention makes it possible to produce GAG in the cytoplasmic compartment of said modified cell. Sulfotransferase substrates, or PAPS, are also produced in the cell cytoplasm. Because of possible co-localization of GAG and PAPS, GAG sulfation is possible in the cytoplasm of said genetically modified cells.

According to still another aspect, the invention relates to a method for producing chondroitin sulfate in a genetically modified cell, said method comprising a first step of GAG production and a second step of GAG sulfation.

GAG sulfation can be carried by the implementation of methods well-known to persons skilled in the art. Chondroitin sulfate synthesis can be can be carried out by chemical or enzymatic sulfation (Ninomiya et al., 2002). GAG sulfation can also be implemented within the genetically modified cell in which GAG is produced, in particular by the presence of endogenous or exogenous genes encoding an enzyme capable of exerting a GAG sulfotransferase activity.

In an even more particular aspect, the invention relates to a method for producing GAG in a genetically modified cell comprising:
1) obtaining a cell comprising at least: an exogenous gene encoding a preferably mammalian enzyme capable of exerting a glycosyltransferase activity on a beta-galactoside substrate, preferably a glucuronyltransferase activity, and the elements enabling the expression of said gene in said cell; a gene encoding an enzyme capable of synthesizing said GAG from glycosyl beta-glucuronide, or the genes encoding the enzymes of the synthetic pathway of said glycosaminoglycan from glycosyl beta-glucuronide, and the elements enabling the expression of said gene(s) in said cell, a gene encoding an enzyme capable of ensuring the exogenous internalization of beta-galactoside by the cell, and the elements enabling the expression of said gene in said cell,
2) culturing said cell in the presence of exogenous beta-galactoside and under conditions compatible with the production of heparosan by the cell, and
3) purifying the GAG produced in step 2).

The glycosaminoglycan from the culture of the genetically modified cell can be purified by any suitable means known to persons skilled in the art. This means will in particular be suited to the production of GAG in the cytoplasm of the genetically modified cell.

In a particular aspect, the invention relates to a method for producing chondroitin in a genetically modified cell, the method comprising:
1) obtaining an *Escherichia coli* strain K12 cell, comprising at least:
   - a gene encoding a mammalian glucuronyltransferase, and the elements enabling the expression of said gene in said cell,
   - a gene encoding a bacterial chondroitin synthase, and the elements enabling the expression of said gene in said cell,
   - a gene encoding a beta-galactoside permease, and the elements enabling the expression of said gene in said cell,
2) culturing said cell in the presence of exogenous beta-galactoside and under conditions compatible with the production of chondroitin by the cell, and
3) purifying by chromatography the chondroitin produced in step 2).

According to another aspect, the invention relates to the use of an *Escherichia coli* cell comprising at least the genes glcA-T, kfoC, kfiD and wbpP for producing chondroitin.

According to another aspect, the invention relates to the use of an *Escherichia coli* cell comprising at least the genes glcA-T, kfiA, kfiB, kfiC and kfiD for producing heparosan.

More particularly, the invention relates to the use of chondroitin obtained by implementing a method according to the invention for synthesizing chondroitin sulfate. The invention also relates to the use of heparosan obtained by implementing a method according to the invention for synthesizing heparosan sulfate.

According to another aspect, the invention relates to the use of GAG obtained by implementing a method of the invention for the preparation of a medicinal product, for regenerating or engineering tissues or for carrying out a diagnostic test. More particularly, the invention relates to the use of chondroitin obtained by implementing a method according to the invention for the preparation of a medicinal product intended for the treatment a disease selected from: cancer, osteoarthritis and inflammation, or a medicinal product intended to be used in tissue regeneration or engineering. In another particular aspect, the invention relates to the use of heparosan obtained by implementing a method according to the invention for the preparation of a medicinal product intended for the prevention of a thromboembolic event or intended to be used as an anticoagulant.

According to another aspect, the invention relates to the use of a GAG obtained by implementing a method according to the invention, preferably chondroitin or heparosan, for the preparation of a food composition or nutritional supplement or for the preparation of a cosmetic product. According to another aspect, the invention relates to the use of chondroitin obtained by implementing a method according to the invention for the preparation of a nutritional supplement.

Other features and advantages of the invention will be apparent in the following examples and figures.

FIGURE LEGENDS

FIG. 2: Diagram of the strategy for synthesizing chondroitin in *E. coli* from exogenous lactose (Lac), with galactose (Gal), glucose (Glc), uridine diphosphate (UDP), glucuronic acid (GlcA), N-acetylgalactosamine (GalNAc), and
  uridine diphosphate-glucose (UDP-Glc),
  uridine diphosphate-glucuronic acid (UDP-GlcA),
  uridine diphosphate-N-acetylgalactosamine (UDP-GalNac),
  uridine diphosphate-N-acetylglucosamine (UDP-GlcNac),
  the *E. coli* gene encoding a GlcNAc transferase (kfiA)
  the *E. coli* gene encoding a glcA transferase (kfiC),
  the *E. coli* gene encoding a UDP-glucose 6-dehydrogenase (kfiD)
  the gene encoding the UDP-N-acetylglucosamine epimerase from *Pseudomonas aeruginosa* (wbpP)
  the gene encoding glucuronyltransferase (glcA-T)
  the gene encoding the enzyme using UDP-GlcA for the synthesis of colanic acid (wcaJ)
  the *E. coli* gene encoding chondroitin polymerase (kfoC)

FIGS. 5A and 5B: Spectra resulting from GPC analysis of chondroitin produced by the recombinant strains. FIG. 5A: Analysis of the chondroitin produced by the recombinant strain KCB2 (average measured size: 17,970 Da, polydispersity: 1.35). FIG. 5B: Analysis of the chondroitin produced by the recombinant strain KCO1 (average measured size: 73,510 Da, polydispersity: 1.42).

EXAMPLES

Example 1: Engineering of Glycosylation in *Escherichia coli*

The *E. coli* K12 strain (called DJ) used to produce chondroitin from exogenous lactose is disclosed in Yavuz et al. (2008), this strain is an *E. coli* DH1 strain (reference ATCC: 68153) modified as indicated in the publication of Yavuz et al. The K12 strain used is transformed by a plasmid having the *E. coli* K4 kfoC gene. The kfoC enzyme uses UDP-GalNac which is provided by the expression of wbpP, the gene encoding a UDP-N-acetylglucosamine epimerase from *Pseudomonas aeruginosa*. The *Pseudomonas aeruginosa* wbpP gene, encoding UDP-Glc epimerase, was also introduced into the bacterium. For the synthesis of glucuronyl-lactose, the GlcA-T enzyme enables the addition of a glucuronic acid (GlcA) on the lactose from UDP GlcA. The gene encoding rat brain glucuronyltransferase (GlcA-T) is also introduced into the bacterium. It is important to have an upstream accumulation of UDP-GlcA. To that end, the strain is transformed with a plasmid containing the kfiD gene. This gene encodes a UDP glucose dehydrogenase present in K5 enabling the synthesis of UDP-GlcA from UDP-Glc. Moreover, the K12 strain was made LacZ- and wcaJ- by deletions. The lacZ gene is part of the lactose operon; it encodes a beta-galactosidase that hydrolyzes lactose to galactose and glucose. Its inactivation prevents the degradation of lactose and thus increases its availability for metabolic synthesis of the product of interest. The wcaJ gene, in turn, encodes an enzyme using UDP-GlcA in the synthesis of colanic acid. Its inactivation enables, in the present case, an accumulation of UDP-GlcA. Moreover, colanic acid being an acidic oligosaccharide, it can interfere during chondroitin purifications, the fact of inhibiting its synthesis is thus all the more beneficial. The lacZ-, wcaJ-K12 strain is called DJ.

The various strains studied are SBP9-24, KCB1 and KCB2 (Table 1).

TABLE 1

Characteristics of the strains studied

| Strain | Host | Plasmids present | Resistances | Comments |
|---|---|---|---|---|
| SBP9-24 | DJ | pACT3-GlcA-T, pBS-kfoC, pBBR-kfiD, pWKS-wbpP | KATC | Reference strain, 4 plasmids present |
| KCB1 | DJ | pBBR-kfiD, pBS-kfoC-GlcA-T, pWKS-wbpP | KAT | 3 plasmids present, GlcA-T gene inserted into a high-copy-number plasmid |
| KCB2 | DJ | pBBR-GlcA-T-kfiD, pBC-kfoC, pWKS-wbpP | KAT | 3 plasmids present, GlcA-T inserted into an average-copy-number plasmid |
| KCO1 | DJ | pBBR-kfiD, pBC-kfoC, pWKS-wbpP | KAT | Control without GlcA-T |
| KCO3 | DJ | pBBR-GlcA-T-kfiD, pBS-empty, pWKS-wbpP | KAT | Control without KfoC |

Strain SBP9-24 is regarded as the reference construction with four plasmids, each carrying a gene of interest. KCB1 and KCB2 contain only three plasmids and differ by the plasmid that carries two genes (pBS-kfoC-GlcA-T for KCB1 and pBBR-GlcA-T-kfiD for KCB2), their difference being that KCB2 has the GlcA-T gene in a plasmid expressed in a lower level than that of KCB1. Two control strains are prepared: KCO1 and KCO3, in order to observe the impact of the expression of GlcA-T (KCO1) and KfoC (KCO3) on the production of chondroitin. The lacZ, wcaJ BL21 strain of *E. coli* is transformed by the plasmids: pBBR-glcAT-kfiD; pBS-kfoC; pWKS-wbpP, is also used.

Example 2: Production of Chondroitin in *E. coli* from Exogenous Lactose

The transformations of *E. coli* K12 are carried out from the K12 strain "DJ" which is lacZ and wcaJ. The plasmids (200 ng for pBBR and pWKS, 100 ng for pBS) are added to 100 µl of competent bacteria. After 15 minutes in ice and heat-shock for 45 seconds at 42° C., 400 pl of SOC medium is added and the whole is incubated for 1 hour at 37° C. After concentration in 100 µA of supernatant, the mixture is plated on a plate containing LBA+glucose (0.1% v/v) and the corresponding antibiotics (0.1% v/v) and incubated at 30° C. overnight.

Composition of the Media $KH_2PO_4$ (5 g/l), $NH_4PO_4$ (5 g/l), citric acid (0.5 g/l), NaOH (0.66 g/l), KOH (1.65 g/l), TMS (7.5 ml/l), glycerol (2.4 g/l). Glucose (17.5 g/l) and $MgSO_4$ (1 g/l) are autoclaved separately. Thiamin (10 mM) and antibiotics (35 mM) are added after autoclaving.

Composition of the Supply

Glycerol (750 g/l), $MgSO_4$ (18 g/l), TMS (37.50 ml/l). The supply is delivered at a flow rate of 9 ml/min during the second phase then at a flow rate of 6 ml/min during the third phase (see Culture preparation).

Culture Preparation

The cultures are grown in 3-liter Applikon fermentors with a total volume of medium of 1.5 liters. During these cultures, several parameters are controlled; oxygen at 40%, temperature at 33 or 28° C. according to the culture phase and pH at 6.80 with ammonia at 30% (10). Culture preparation is divided into several phases.

The first phase corresponds to a growth phase with the provision of a carbon source, glucose. The latter enables catabolic repression, thus the lac operon, used as promoter in the plasmids carrying the genes of interest, is inhibited. This prevents any production before induction and thus promotes bacterial growth. During this step, the temperature of the culture is maintained at 33° C. This step is concluded when all the glucose and glycerol present in the initial culture medium has been consumed.

The second phase is an induction phase with the provision of a supply containing glycerol as carbon source to replace the glucose of the initial medium. The supply is administered at a flow rate of 9 ml/min. After a test for reaction of the culture to the supply (stopping the supply and observing an increase in oxygen), the culture temperature is decreased to 28° C. After a second test for response to the supply at this temperature, induction of the expression of the genes of interest was achieved by injecting 50 mg/l IPTG. At that time, the exogenous precursor necessary to the synthesis chain, lactose, is also provided in the medium at a concentration of 1.6 g/l.

The third and last phase is started 5 hours after induction by reducing the supply flow rate (6 ml/min) so as to slow bacterial growth while continuing to provide the energy supply necessary to the production of the polysaccharide of interest.

During the cultures, 1.5 ml samples are taken 1 hour after induction (1 h), the day after induction (24 h), the third day one hour after the second lactose injection (48 h) and the last day before stopping the cultures (72 h). After centrifugation for 5 minutes at 13,000 g, the supernatant is set aside (extracellular fraction) while the pellet is taken up in 1 ml of distilled water then placed in a 100° C. water bath for 10 minutes. After resuspension and centrifugation for 3 minutes at 13,000 g, the pellet contains bacterial debris and the supernatant corresponds to the intracellular fraction. The fractions resulting from these samplings are analyzed on a thin layer of silica (TLC) by migration in n-butanol/acetic acid/water (2:1:1) buffer for 30 minutes. The standard used during these TLC is a GlcA-Lac/lactose mixture. The TLC are developed with a mixture of ethyl acetate (100 ml), diphenylamine (2 g), aniline (2 ml), 85% phosphoric acid (10 ml) and hydrochloric acid (1 ml).

After stopping the fermentors, the culture is collected then centrifuged for 20 minutes at 7,000 rpm in order to separate the bacteria from the extracellular medium. The bacterial pellets, taken up in 500 ml of $H_2O$, are subjected to heat treatment (20 minutes in an autoclave at 100° C.) so as to lyse the bacteria. To finish, the pellets are resuspended and ground then centrifuged for 20 minutes at 7,000 rpm so as to remove the bacterial debris and retain only the supernatant which corresponds to the intracellular fraction of the bacteria. The supernatants collected following the first centrifugation correspond to the extracellular fractions.

Purification and Analysis of Sugars

First, the pH of the fractions is adjusted to 3.5 by treatment with cation-exchange resin (Amberlite IR-120) which precipitates the proteins, the fractions are centrifuged for 20 minutes at 7,000 rpm in order to remove the protein precipitate and the supernatants had their pH adjusted to 6.5 by treatment with anion-exchange resin (Dowex 66). Second, 500 ml of the fractions is subjected to ethanol precipitation (3 volumes of 96% ethanol per 1 volume of fraction) so as to precipitate the chondroitin. After 3 hours at 4° C., the mixture is centrifuged for 20 minutes at 7,000 rpm and the pellet solubilized in 80 ml of water.

The fractions thus purified are then assayed for uronic acid (UA) and for amino sugar by colorimetric assay, respectively by the method of Blumenkrantz (1973) with glucuronic acid (GlcA) as standard and that of Morgan (1955) with N-acetylgalactosamine (GalNAc) as standard. These assays made it possible to obtain a theoretical concentration of chondroitin by means of the following relationships:

$$Q_{chondroitin} = (Q_{UA}/M_{gIca}) \times (M_{QalNAc} - 18) + Q_{UA}$$

$$Q_{chondroitin} = (Q_{amino\ sugars}/M_{GalNAc}) \times (M_{GlcA} - 18) + Q_{amino\ sugars}$$

The products thus obtained after purification were frozen in liquid nitrogen then lyophilized so as to obtain a dry mass weighed and used for the characterization of the product.

The various culture products are analyzed by gel permeation chromatography (GPC-SEC). The GPC-SEC is carried out on Shodex 802/803 columns eluted with 0.1 M sodium nitrate ($NaNO_3$) at a flow rate of 0.5 ml/min. Detection is triple with a Waters refractometer, a multiangle light scattering (MALS) detector with 18 angles (Wyatt) and a dn/dc of 0.142 (WO2012/089777). The data are processed with the Astra software (Wyatt).

Results

Comparison of the Various Recombinant Bacterial Strains

Several recombinant strains are compared: SBP9-24, KCB1 and KCB2, in order to select the most advantageous strain in terms of quality and amount for producing the polysaccharide of interest. To that end, it was decided first to compare these strains in terms of synthesis of the chimeric acceptor (GlcA-Lac).

Lactose must be correctly internalized in the bacterium to enable sufficient intracellular accumulation of GlcA-Lac. The latter could then be recognized as an acceptor by KfoC. Thus, during the cultures of the various recombinant strains, several samples were taken in order to evaluate by TLC the concentrations and distribution of lactose and GlcA-Lac.

It is possible to differentiate the strains on certain points. First, for rate of lactose consumption, the three-plasmid strains, KCB1 and KCB2, consumed all the lactose from the first day after 24 to 48 hours, which is not the case for SBP9-24. In view of this result, it was decided to carry out a second lactose injection (1.6 g/l) at the end of 48 hours, which will also be the case for all the other cultures. This observation agrees with a second which is that lactose is internalized much more quickly by strains KCB1 and 2 than by strain SBP9-24 where extracellular lactose is observed longer after an injection. In the case of the three strains, lactose is observed to metabolize to GlcA-Lac, a sign that metabolic synthesis has begun. It seems, however, that the three-plasmid strains perform better in terms of GlcA-Lac production (high rate of lactose consumption, greater presence of GlcA-Lac at the end of the culture).

Second, the strains are compared in terms of the production of chondroitin itself, by means of colorimetric assays of uronic acids and amino sugars, making it possible to quantify the production of chondroitin for each strain.

Figure 3:
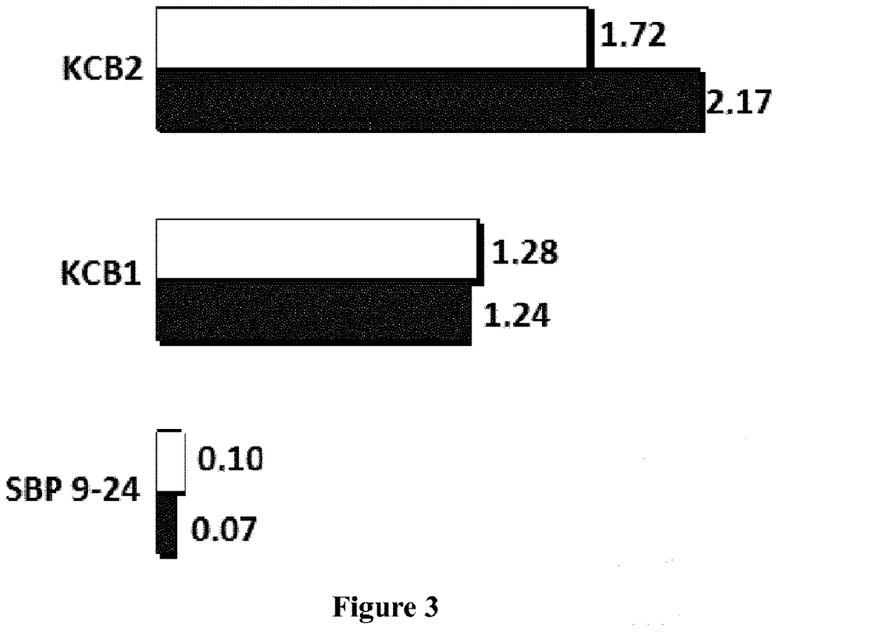
FIG. 3: Measurement of uronic acids (black bars) and amino sugars (white bars) by colorimetric assays in intracellular fractions of the recombinant strains, with, from top to bottom, KCB2, KCB1 and SBP9-24. The amount of uronic acids (UA) and of amino sugars is indicated in g/l.

Increased production of uronic acids and amino sugars is observed in the three-plasmid strains (FIG. 3). One possible reason for this difference is the fact that strain SBP9-24 grows with more difficulty than the two three-plasmid strains. Between KCB1 and KCB2, it seems that KCB2 produces more, a sign that GlcA-T expression does not need to be very high since this enzyme is encoded in an average-copy-number plasmid (pBBR) in KCB2 and not in a high-copy-number plasmid (pBS) in KCB1.

It thus seems that the recombinant strain KCB2 is the most productive in chondroitin from the chimeric acceptor. It is thus this strain which was selected to carry out the production and characterization of the chondroitin.

Analysis of Chondroitin Production by Strain KCB2

It is important to show that in KCB2 chondroitin is produced from the chimeric acceptor, glucuronyl-lactose. To that end, a control strain, KCO1, is constructed, which does not have the gene encoding GlcA-T. Thus, this negative control cannot transform lactose into GlcA-Lac. That gives an indication of chondroitin production when glucuronyl-lactose is not present.

The absence of glucuronyl-lactose in KCO1 results in a lower concentration of uronic acid and of amino sugar (FIG. 4), and thus of chondroitin (0.5 g/l), in the intracellular fraction. This amount is about three times lower than that produced in KCB2 (1.7 g/l). Thus, it appears that in the absence of glucuronyl-lactose, the synthesis of chondroitin occurs nevertheless, necessarily from an endogenous acceptor.

Figure 4:
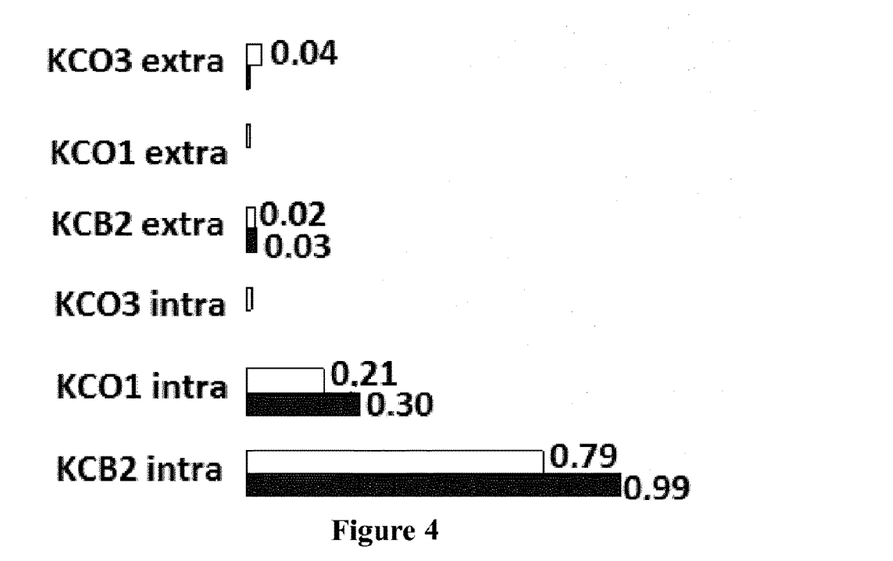
FIG. 4: Measurement of uronic acids and amino sugars by colorimetric assays in intra and extracellular fractions of the recombinant strains, with, from top to bottom: extracellular fraction of KCO3, KCO1 and KCB2, intracellular fraction of KCO3, KCO1 and KCB2. The amount of uronic acids (UA, black bars) and of amino sugars (white bars) is indicated in g/l.

The production of chondroitin in the recombinant strain KCB2 is also compared with that in another control: strain KCO3. This strain lacks the gene encoding KfoC. Its absence in strain KCO3 results in the virtual absence of uronic acid and amino sugar both in the homologous fraction and extracellularly (FIG. 4). From the TLC of the culture samples, it is observed that the production of glucuronyl-lactose indeed takes place. Thus, KfoC is essential to the synthesis of chondroitin, even if the chimeric acceptor is present.

Characterization and Analysis of Chondroitin

It was shown above that in the absence of glucuronyl-lactose, chondroitin is synthesized from an endogenous acceptor. That is consistent with the results of synthesis in vivo shown in various publications. However, the GPC analysis gives a size of chondroitin in KCB2 (produced from glucuronyl-lactose) of 17.5 kDa (FIG. 5A) whereas the publications report a size of synthesized chondroitin (in K4 or K5) in the vicinity of 100 to 600 kDa. Consequently, one can wonder whether the small size obtained in KCB2 is due to the properties of strain K12 or the fact of initiating the synthesis by a different acceptor. To answer this question, a GPC analysis is also carried out on the purified products of KCO1 (control strain without GlcA-T) and the measured size of the chondroitin produced is about 73 kDa (FIG. 5B). Thus, the presence of glucuronyl-lactose, as a precursor for the synthesis, results in the production of a different chondroitin, smaller than that produced from the endogenous acceptor.

Figure 5A:
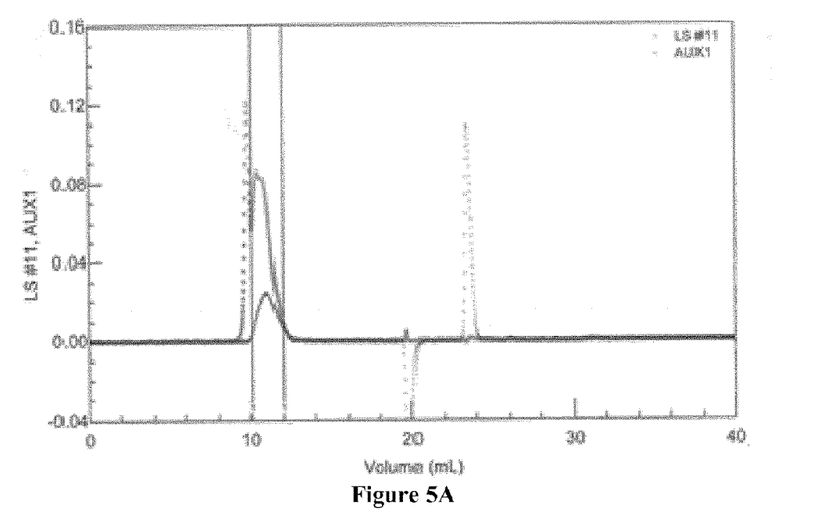
Figure 5B:
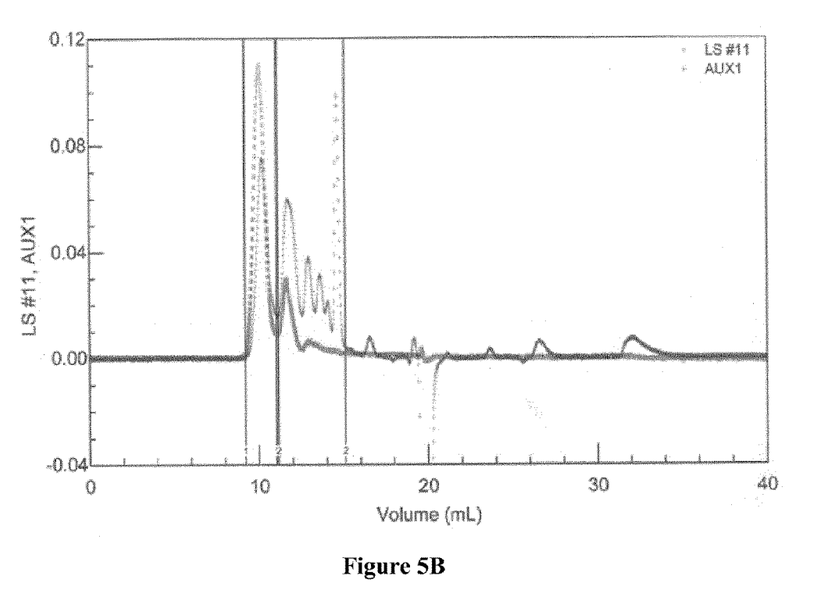

Another remarkable fact is that in the presence of glucuronyl-lactose, the 73 kDa chondroitin is completely absent (size between 15 and 20 kDa, polydispersity of 1.35) (FIG. 5A). Two hypotheses can be formulated to explain this observation. The first is that the production of glucuronyl-lactose results in a greater presence of substrate for KfoC than when the endogenous acceptor is used alone. Thus, the KfoC enzyme restarts synthesis more often from oligosaccharides and precursor instead of continuing polysaccharide elongation. The result is thus a decrease in the average size of the chondroitin produced.

The second hypothesis is that the membrane environment stabilizes enzyme chondroitin coupling to the benefit of polysaccharide polymerization. Indeed, in the wild, chondroitin synthesis takes place in the perimembrane space, the endogenous acceptor being membranous. There, KfoC has membrane complex support for the synthesis of chondroitin whose roles are poorly understood (Whitfield, 2006). Glucuronyl-lactose being cytoplasmic, the synthesis, in the case of this study, thus takes place far from the membrane. This cytoplasmic positioning of the synthesis could have an impact on elongation of the chondroitin.

The production of chondroitin in a nonpathogenic recombinant strain of E. coli is thus advantageous because it provides, compared to the other modes of production, ease of handling. Qualitatively, the chondroitin obtained is smaller in size than that obtained by other means (15 kDa versus around 100 kDa in culture and 20 kDa in vitro). This mode of production is also advantageous in terms of the amount produced, which reaches 1.7 g/l, whereas the highest productions in a fermentor in E. coli K4 are reported as having a production of 1.4 g/l (Schiraldi et al., 2010).

The chondroitin produced was analyzed by NMR. The structure of the repeating unit [GlcAb-3GalNAcb-4] is confirmed by $^1$H and $^{13}$C NMR analysis, the results of which are consistent with those published in the literature for defructosylated K4 polysaccharide and chondroitin from Pasteurella multocida. The proton NMR spectrum shows signals at 4.55, 3.43 and 3.64 ppm, which correspond to H-1, H-3, and H-2 of the Glcp-UA residue. The signals at 4.18 and 2.08 ppm correspond to H-4 and H(Ac) of the Galp-NAc residue. The carbon NMR shows the assignments characteristic of the N-acetamido group at 23.91 and 176.22 ppm. One also finds the assignment characteristic of the C-6 of the Glcp-UA residue at 175.61 ppm.

Example 3: Production of Chondroitin in E. coli from Exogenous Beta-methylgalactoside The bacterial strains are prepared and grown according to the protocol disclosed in Example 2, except for the fact that the exogenous beta-galactoside consists in beta methylgalactoside, added in the amount of 4.2 grams in the culture medium. The amount of beta-methylgalactoside added to the medium is identical to the amount of lactose added in Example 2, taking into account the different molar masses of the two products.

The chondroitin fraction produced has a size of 37-61 kDa, i.e. a size smaller than that of the chondroitin obtained in the absence of exogenous acceptor, but larger than that obtained in the presence of lactose.

Example 4: Production of Heparosan by an Escherichia coli K12 Strain in the Presence of Intracellular Glucuronyl-Lactose The production of recombinant heparosans is a major issue because they can be used as precursors of heparin, in particular if they have a small size of about 15-20 kDa (Manzoni et al., 1996). Heparosan is formed of a series of [-4)-β-GlcA-(1-4)-α-GlcNAc-(1]. Its biosynthetic pathway is similar to that of K4 polysaccharide and the genes associated with exportation are the same (Whitfield, 2006).

An E. coli K12 strain was modified to produce heparosan (Barreteau et al., 2012). This strain expresses the E. coli kfiABCD genes (X77617 of 23 Oct. 2008), the presence of which is necessary and sufficient to produce heparosan intracellularly, having a size of about 80 kDa. This strain was now transformed by a plasmid expressing mouse glucuronyltransferase enabling the intracellular synthesis of glucuronyl-lactose in the presence of lactose. To follow the result of this study, a first expected clue of the handling of glucuronyl-lactose by the polymerases is the synthesis of a smaller polysaccharide, if one refers to the results obtained with chondroitin for which it is indeed the case.

The same strain was grown in 2-liter fermentors in the presence (7.5 g of lactose added to the supply over 3 days) and in the absence of extracellular lactose.

The results are as follows:
Assay of uronic acids of the ethanol-precipitated fraction:
Without addition of lactose: 825 mg total (about 0.8 g/l heparosan)
With addition of lactose: 444 mg total (about 0.45 g/l heparosan)
Size analysis of the recombinant heparosans:
The fractions were analyzed by SEC-MAL in order to obtain the size and the dispersity of the heparosans produced. However, the large presence of aggregates necessitated a subsequent step of purification by ion-exchange chromatography.

The "without lactose" fraction was passed through DEAE-A25 and a retained fraction representing 40% of the total deposited, called SL, was collected.

Figure 6A:
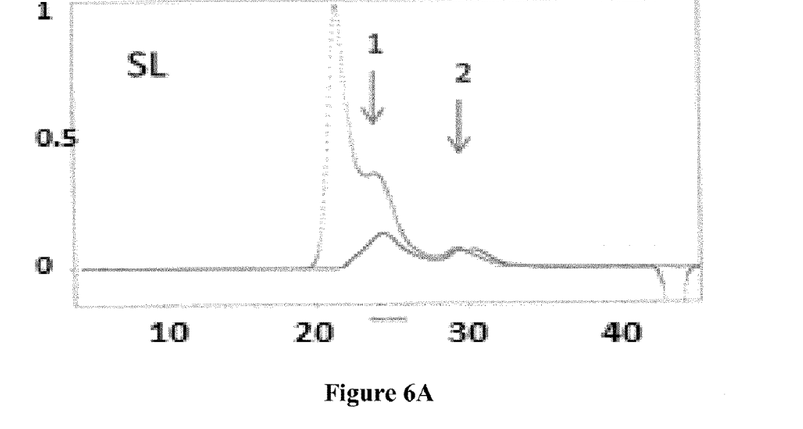
FIGS. 6A to 6C: Spectra resulting from size-exclusion chromatography-multiangle light scattering (SEC-MALS) analysis of the SL (FIG. 6A), AL1 (FIG. 6B) and AL2 (FIG. 6C) fractions obtained during the production of heparosan.
Figure 6B:
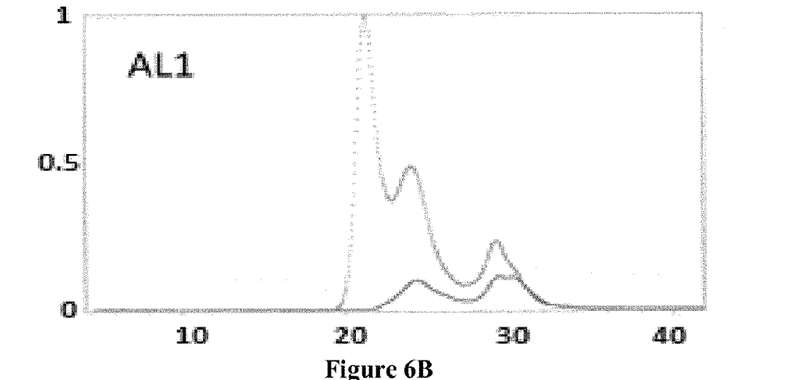
Figure 6C:
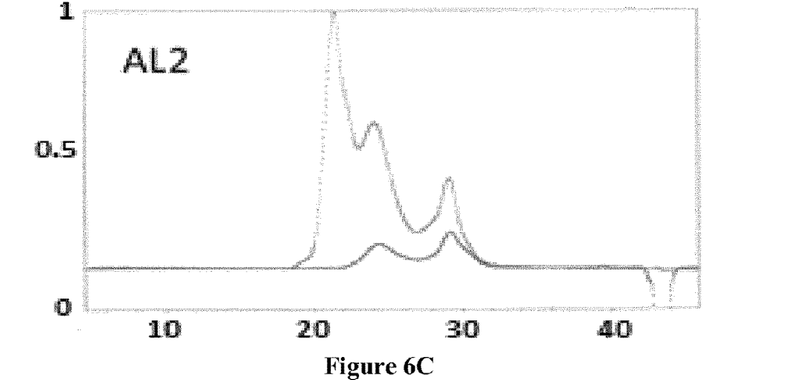

The "with lactose" fraction was passed through DEAE-A25 and a retained fraction, called AL1, representing only 20% of the total deposited was collected, a difference in yield which could be due to the nature of the heparosans produced. It was decided to use a stronger exchanger of the QAE-A25 type. This made it possible to collect a second fraction, called AL2, representing 30% of the total of the initial fraction. Fractions SL, AL1 and AL2 were analyzed by SEC-MALS with no aggregate formation (FIGS. 6A with 6C). The characteristics of the analyzed peaks are as follows:

TABLE 2

Characteristics of the heparosans produced

| | | Peak 1 | Peak 2 |
|---|---|---|---|
| SL | % total (RI detection) | 67 | 33 |
| | Mw (Da) | $7.57 \times 10^4$ | $2.05 \times 10^4$ |
| | Mz (Da) | $1.06 \times 10^5$ | $2.26 \times 10^4$ |
| | Polydispersity (Mw/Mn) | 1.4 | 1.1 |
| AL1 | % | 44 | 68 |
| | Mw (Da) | $5.49 \times 10^4$ | $1.87 \times 10^4$ |
| | Mz (Da) | $6.43 \times 10^4$ | $2.17 \times 10^4$ |
| | Polydispersity (Mw/Mn) | 1.4 | 1.3 |
| AL2 | % | 49 | 51 |
| | Mw (Da) | $6.94 \times 10^4$ | $2.72 \times 10^4$ |
| | Mz (Da) | $7.35 \times 10^4$ | $2.89 \times 10^4$ |
| | Polydispersity (Mw/Mn) | 1.4 | 1.06 |

Fraction SL is essentially composed of a polymer whose size has already been observed (Barreteau et al., 2012). However, it also has a fraction of smaller size which represents about 30% of the total. Fractions AL1 and AL2 are distinguished by an enrichment of the smallest fraction (peak 2), which represents at least 50-70% of the total based on refractometric quantification. Intracellular production in a recombinant E. coli K12 strain capable of synthesizing recombinant heparosan induced a change in the amount and the characteristics of the heparosans produced. The result is an enrichment of a small heparosan about 20 kDa in size.

Example 5: Production of Heparosan in an Escherichia coli K12 Strain in the Presence of Intracellular Glucuronyl-Lactose The genes specific to the synthesis of heparosan from E. coli belong to the cluster of operon K5 and are: kfiA, encoding a GlcNAc transferase; kfiB, whose role is unknown; kfiC, encoding a glcA transferase; kfiD, encoding a UDP-Glc dehydrogenase.

The aim of this study is the metabolic engineering of E. coli K12 in order to enable a synthesis of heparosan from a beta-glucuronidated exogenous cytoplasmic acceptor coming from the action of mouse GlcA-T (encoded by the glcAT gene) on a beta-galactoside. Several strains are prepared, disclosed in the table below. Strain HB5 is disclosed in Barreteau et al. (2012).

TABLE 3

Characteristics of the prepared strains

| | | Plasmids | | | | | |
|---|---|---|---|---|---|---|---|
| Strain | Host | pBBR-kfiAB Tet, low copy | pSU-kfiCD Cm, low copy | pBBR-GlcAT-kfiD Tet, low copy | pBBR-kfiABCD Tet, low copy | pBS-kfiAC Amp, high copy | pSU-GlcAT Cm, low copy |
| HB5 | DJ | + | + | − | − | − | − |
| KHB1 | DJ | − | − | + | − | + | − |
| KHB2 | DJ | − | − | − | + | − | + |
| KHB3 | DJ | − | − | − | + | + | + |

A first strain, KHB1, is prepared, expressing the kfiA and kfiC genes encoding the two glycosyltransferases involved in the synthesis of heparosan in a high-copy-number pBluescript (pBS) plasmid, alongside the kfiD (synthesis of UDP-GlcA) and glcAT (mouse glucuronyltransferase) genes. This strain does not express KfiB, insofar as it was shown that this protein promotes the anchoring of KfiC to the membrane, where the endogenous membrane acceptor is located (Hodson et al., 2000). The aim here being to synthesize heparosan from glucuronyl-lactose, one can think that this membrane association is no longer necessary, or is even harmful, because the location of the endogenous acceptor is also membranous. Two cultures are prepared with or without added lactose. Lactose is added in the amount of 7.5 g (for 2 liters of culture) continuously over the 3 days of supply after induction. The results are obtained after ethanol precipitation of the intracellular fraction and the assay of uronic acids. No heparosan synthesis was obtained, whether in the presence or in the absence of lactose (Table 4). Nevertheless, these results corroborate those of the publication of Hodson et al. (2000), which mentions the crucial role of KfiB in the stability of the heparosan synthase enzyme complex.

It is thus decided to express the set of kfiABCD genes, while adding thereto the expression of mouse glucuronyl-transferase. To that end, the four kfiABCD genes are cloned into the same low-copy plasmid, in order to enable co-expression with the glcA-T gene in a second, also low-copy-number pSU plasmid. The strain, named KHB2, is grown in the presence and the absence of lactose. In the absence of lactose, this strain produces an amount of heparosan comparable with that obtained with strain HB5 published previously (Barreteau et al., 2012). This is consistent with the fact that these two strains are comparable, including in terms of the levels of expression of the four kfiABCD genes, all cloned into low-copy-number plasmids. The absence of lactose deprives the bacterium of the potential acceptor glucuronyl-lactose, which explains the similar results with the reference strain. In the presence of lactose, the result is a decrease in heparosan production, but the interesting fact is that one observes an enrichment of the small heparosan fraction, suggesting that the heparosan synthase complex has taken glucuronyl-lactose as polymerization acceptor, insofar as this phenomenon is observed with the synthesis of chondroitin from glucuronyl-lactose. These results show a low production yield of heparosan, and a polysaccharide fraction obtained composed of two fractions of different sizes.

A new strain, named KHB3, is then prepared. KHB3 is in fact a strain for which the level of expression of the kfiA and kfiC genes is increased, compared to other genes, in order to increase the level of glycosyltransferase activities in relation to KfiB expression. The results are surprising: in the presence of lactose, heparosan production is doubled in relation to the reference strain, HB5, which is completely novel. This result was confirmed by growing this same strain in the presence of lactose-allyl. Without lactose, there is no increase in heparosan production, despite the higher expression of the heparosan synthase enzymes KfiA and KfiC. Also for chondroitin, we had observed that the addition of lactose increased the production yield. This suggests that the concentration of endogenous membrane acceptor is a factor limiting the production of chondroitin and heparosan in the Escherichia coli K-12 strain. The abundant presence of a cytoplasmic auxiliary acceptor would lift this limitation. The low expression of KfiB is apparently enough to stabilize the KfiA/KfiC enzyme complex despite the higher expression of the latter.

Figure 7:
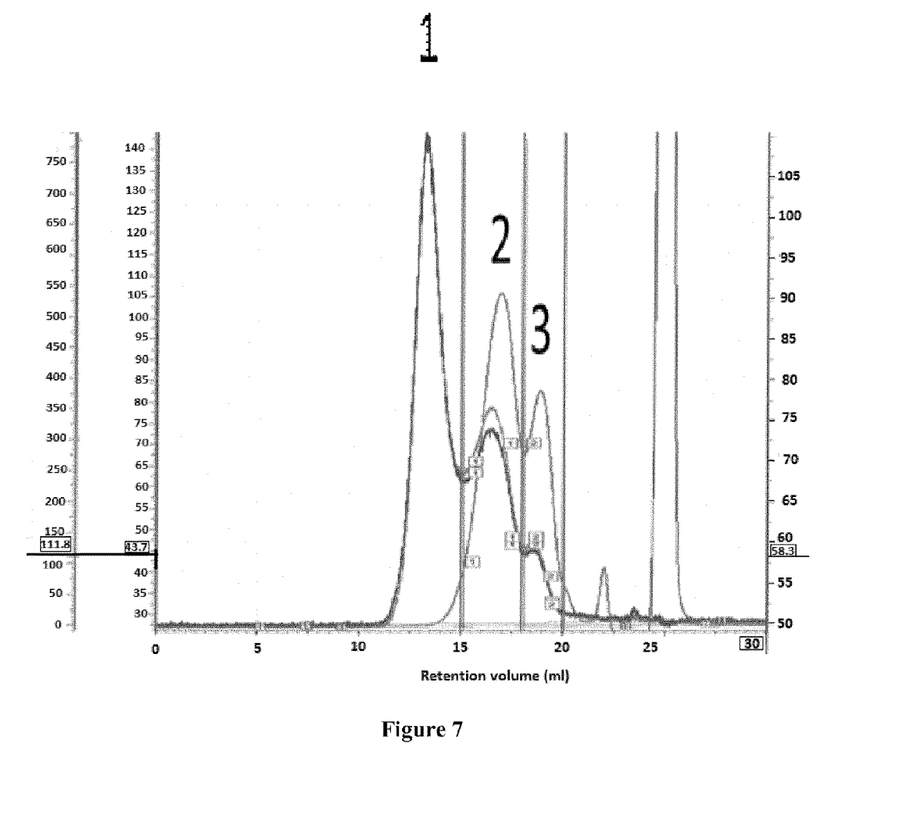
FIG. 7: Spectra resulting from GPC (SEC-MALS) analysis of the heparosan fraction produced in strain KHB3 from allyl-lactose. Peak 1, aggregates; peak 2, Mw 52,740 Da, Mw/Mn 1.17; peak 3, Mw 22,346 Da, Mw/Mn 1.09.

The GPC analysis was carried out on the fraction prepared from allyl-lactose (FIG. 7). It is composed of two polysaccharide species, 53 kDa and 22 kDa in size, having very low polydispersity. These sizes are smaller than what is normally produced with the kfi genes, in our laboratory and also in the literature and existing patents. This phenomenon is consistent with what is observed with the production of chondroitin, where a decrease in size in the presence of glucuronyl-lactose is also observed.

TABLE 4

Amount of heparosan produced (expressed as g/l of culture).

| Strain | Without lactose | With lactose | With allyl lactose |
|---|---|---|---|
| HB5 | 1.2 | Not performed | Not performed |
| KHB1 | Not detected | Traces | Not performed |
| KHB2 | 0.9 | 0.45 | Not performed |
| KHB3 | 0.84 | 2.6 | 2.7 |

BIBLIOGRAPHICAL REFERENCES

Cimini et al. (2010) *Appl. Microbiol, and Biotechnol,* 85(6): 1779-1787.
Jin et al. (2011) *Biosci. Biotechnol. Biochem.,* 75(7), 1283-1289.
Yamada and Sugahara (2008) *Current Drug Discovery Technologies,* 5, 289-301.
Zanfardino et al. (2010) *Microbiol. Cell Factories,* 9:34.

Wang et al. (2011) *Bioengineered Bugs*, 2:1, 63-67 (January/February)
Schiraldi et al. (2010) *Appl. Microbiol, and Biotechnol*, 87:1209-1220.
Inoue et al. (1990) *Gene*, 96:23-28.
Yavuz et al. (2008) *Glycobiology*, 18(2):152-157.
Ninomiya et al. (2002) *J. Biol. Chem.*, June 14; 277(24): 21567-75.
Priem et al. (2002) *Glycobiology*. Vol. 12 no. 4 pp. 235-240.
Krahulec et al. (2005) *Molecular Biology*, 30:129-134.
Kakuda et al. (2004) *J. Biol. Chem.*, 279 (21), pp 22693-22703.
Whitfield (2006) *Annual Review of Biochemistry*, 75:39-68.
Morgan et al. (1955) *Biochem. Journal*, 61(4):586-589.
Blumenkrantz et al. (1973) *Analytical biochemistry*, 54:484-489.
Manzoni et al. (1996) *J. Bioactive and Compatible Polymers*, Vol. 11, p 301
Barreteau et al. (2012) *Carbohydrate Research*, 1:360:19-24.
Hodson et al. (2000) *J. Biol. Chem.*, 275(35): 27311-5.

The invention claimed is:

1. A method for producing glycosaminoglycan (GAG) from an exogenous beta-galactoside substrate in a genetically modified cell, said method comprising:
   a) obtaining a cell comprising at least
      i) an exogenous gene encoding a beta-galactosyltransferase, and the elements enabling the expression of said gene in said cell and the synthesis of glycosyl beta-galactoside,
      ii) a gene encoding an enzyme capable of synthesizing said glycosaminoglycan from glycosyl beta-galactoside and the elements enabling the expression of said gene(s) in said cell, and
      iii) a gene encoding an enzyme capable of ensuring the internalization by the cell of exogenous beta-galactoside, and the elements enabling the expression of said gene in said cell;
   b) culturing said cell in the presence of exogenous beta-galactoside and under conditions compatible with the production of said glycosaminoglycan by said cell; and
   c) isolating said produced glycosaminoglycan.

2. The method according to claim 1, wherein said beta-galactosyltransferase is a mammalian glucuronyltransferase.

3. The method according to claim 1, wherein the beta-galactosyltransferase is a mouse glucuronyltransferase.

4. The method according claim 1, wherein said cell further comprises a gene encoding an enzyme capable of synthesizing UDP-GlcA from UDP-Glc, and the elements enabling the expression of said gene in said cell.

5. The method according to claim 4, wherein said enzyme capable of synthesizing UDP-GlcA from UDP-Glc is a UDP-glucose dehydrogenase.

6. The method according to claim 4, wherein the enzyme capable of synthesizing UDP-GlcA from UDP-Glc is a UDP-glucose dehydrogenase encoded by the kfiD gene of *E. coli* K5.

7. The method according to claim 1, wherein said cell further comprises a gene encoding an enzyme capable of synthesizing UDP-GalNAc, and the elements enabling the expression of said gene in said cell.

8. The method according to claim 1, wherein said cell is selected from bacteria and eukaryotic organisms.

9. The method according to claim 8, wherein said bacterium is an *Escherichia coli* nonpathogenic strain bacterium.

10. The method according to claim 1, wherein said glycosaminoglycan is chondroitin.

11. The method according to claim 1, wherein said glycosaminoglycan is heparosan.

* * * * *

SEQUENCE LISTING

```
<160> NUMBER OF SEQ ID NOS: 1

<210> SEQ ID NO 1
<211> LENGTH: 1692
<212> TYPE: DNA
<213> ORGANISM: Escherichia coli

<400> SEQUENCE: 1
atgatgaata aattagtgct agtcggacat cctggctcaa agtatcagat agttgaacat      60
tttttgaaag aaattggcat gaactcacca aattattcta caagtaataa aatttcccca     120
gaatatatca ccgcttcatt atgtcaattt tatcaaacac cagaagttaa tgatgtagta     180
gatgagagag aattctcagc tgttcaagtc tcaaccatgt gggatagcat ggttcttgaa     240
ctaatgatga acaatctaaa taacaaactt tgggggtggg cagatccatc tataatattt     300
tttcttgatt tttggaaaaa tatagataaa agcataaaat tcatcatgat atatgatcac     360
cctaaatata atttaatgcg ttcagtaaat aatgcccctc tctctttaaa tataaataat     420
agtgtagata actggattgc atataataaa agattgcttg atttttttt ggagaataaa      480 gaacgatgtg tgttgattaa ttttgaggcg tttcaaagca ataagaaaaa tattataaag     540
ccattgagta atattataaa aatagataat ctaatgtctg cgcattacaa aaattcaata     600
ttgtttgatg tggttgagaa taatgattat acaaaatcaa atgaaattgc cctgcttgaa     660
aaatatacaa ctttattttc tttaagtgca aatgagactg aaattacatt taatgataca     720
aaggttagtg agtacttagt atctgaatta ataaaagaaa gaaccgaggt tctgaagctt     780
tataatgagt tacaagccta tgcaaaccta ccttatatag aaacatcgaa agataacgtt     840
tcggctgagg ctgcattatg ggaggtagtc gaagagagaa attctatctt caatattgta     900
tctcatttgg tgcaagagtc aaaaaagaag gatgcagata ttgaattgac taaatctata     960
tttaagaaaa gacaattttt attattgaac aggattaatg agctaaaaaa agaaaaggaa    1020
gaggtaatta aactttcaaa aataaatcac aacgatgttg tgagacaaga aaaatatcca    1080
gatgatattg aaaaaaaat aaatgacata cagaaatatg aagaagagat aagcgaaaaa    1140
gaatcaaaac tcactcaggc aatatcagaa aaagaacaga ttttaaaaca attgcataaa    1200
tatgaagaag agataagcga aaaagaatca aaactcactc aggcaatatc agaaaaagaa    1260 cagatttaa aacaattgca tatagtgcaa gagcagttgg aacactattt tatagaaaat    1320
caggaaatta aaagaaact tccacctgtg ctatatggag cagctgagca gataaaacaa    1380
gagttaggtt atcgacttgg ttatattata gtctcgtatt ctaaatccct caagggatt    1440 attaccatgc catttgcact tatccgtgag tgtgttttttt aaaaaaaacg taagaagagt    1500
tatggcgttg atgtgccact ctatttatat gctgatgctg ataaggctga aagagttaag    1560
aaacatttat cttatcaatt agggcaggct attatctcca gtgctaattc gatatttgga    1620
ttcattaccc ttccattaa gttaattgtt gttgtttata aatataggag agctaaaatc    1680
```

```
aagggctgtt aa                                                              1692
```